United States Patent [19]

Hebbard

[11] Patent Number: 5,595,569
[45] Date of Patent: Jan. 21, 1997

[54] SPOON SHAPED TICK REMOVER

[76] Inventor: Rick Hebbard, 97 Spruce La., Dover, N.H. 03820

[21] Appl. No.: 301,600

[22] Filed: Sep. 7, 1994

[51] Int. Cl.⁶ .................................................. A61B 19/00
[52] U.S. Cl. ............................................................ 606/131
[58] Field of Search .............................. 30/141, 145–150, 30/324, 325; 606/131, 1, 205–211, 133

[56] References Cited

U.S. PATENT DOCUMENTS

| | | | |
|---|---|---|---|
| D. 47,443 | 6/1915 | Villemain | 30/149 |
| 2,647,310 | 8/1953 | Yolles | 30/324 |
| 4,213,460 | 7/1980 | Weiner | 606/131 |
| 4,535,538 | 8/1985 | Nelson | 30/147 |
| 4,938,764 | 7/1990 | Glaberson | 606/131 |
| 5,078,729 | 1/1992 | Eichhorn | 606/210 |
| 5,116,347 | 5/1992 | Butler | 606/131 |
| 5,246,449 | 9/1993 | Webster | 606/131 |

FOREIGN PATENT DOCUMENTS 1126617  11/1956  France ..................................... 30/325

*Primary Examiner*—Stephen C. Pellegrino
*Assistant Examiner*—Glenn Dawson
*Attorney, Agent, or Firm*—Lee A. Strimbeck, Esquire

[57] ABSTRACT

The invention is a spoon-shaped device for removing ticks from pets and other hosts. The outer or leading edge of the spoon bowl has a beveled V-shaped notch of a size to permit the bowl to be passed between the tick and the skin of the host until the scoop engages the tick underneath its body on three sides. A further forward sliding motion of the notched area along the skin releases the tick entirely.

7 Claims, 1 Drawing Sheet

SPOON SHAPED TICK REMOVER

FIELD OF THE INVENTION

The present invention is a device for removing parasites such as ticks from household pets, livestock, people or similar types of hosts. More particularly the present invention is a spoon-shaped member that has a notch cut into it that can be manipulated to engage and remove the parasite.

BACKGROUND OF THE INVENTION

The removal of ticks and like parasites from the skin of man and animals should be done with care. Ticks have long been a problem and recently have become more so with the advent of Lyme Disease. Ticks embed their heads into the host's skin and remain attached while feeding on the host's blood. If one manually attempts to pull the tick off, the ticks head or mouth parts may remain embedded in the skin. This may result in infection besides irritation. Also if the tick's body is squeezed in the process of removing it, it may rupture or regurgitate which could cause transfer of disease as well as infection of the wound. As noted below there have been many devices proposed for the removal of ticks, but most are not satisfactory for one reason or another: cost, complexity, lack of effectiveness, or failure to remove the ticks head.

The present invention is a simple, quite inexpensive, manually operated tool for removing ticks. It is slid along the host's skin underneath the tick's body and used to pull the tick free without the need for the fingers to touch the tick's body.

PRIOR ART

A search turned up the following patents pertaining to tick removal devices none of which suggests the particular device disclosed and claimed herein:

| U.S. Pat. No. | Issue Date | Inventor |
|---|---|---|
| 4,938,764 | 7/3/90 | Glaberson |
| 5,078,729 | 1/7/92 | Eichhorn |
| 4,976,718 | 12/11/90 | Daniell |
| 4,303,268 | 12/1/81 | Davidson |
| 5,116,347 | 5/26/92 | Butler |
| 5,002,323 | 3/26/91 | Idsund |
| 4,748,767 | 6/7/88 | Sandels |
| 4,442,837 | 4/17/84 | Keatly |

THIS INVENTION

The present invention is a device for removing blood sucking parasites such as ticks from a host. It comprises a spoon-shaped member having a handle with a scoop at one end. The outer end of the scoop has a notch of a size to permit the spoon to be passed between the parasite and the skin of the host until the scoop engages the parasite underneath the parasite's body on three sides, i.e. the apex of the notch frames the tick. A further forward sliding motion of the notched area along the skin releases the tick entirely. None of the tick's mouth parts are left behind as the tick remover draws the tick upward from the skin. The tick can then simply be tipped out of the cup and disposed of without need to touch it.

Preferably the scoop is hemispherical in shape and the notch in its outer edge is V-shaped extending from the rim of the scoop downwardly approximately 45 degrees or so. The edges of the notch are beveled on the inside, preferably, so as to give the notch a sharp leading edge and to draw the tick upward.

This tick removing device can readily be injection molded from a plastic and is very inexpensive. Its length overall usually will be in the range of 3 to 5 inches and the scoop will have a diameter in the range of 0.4 to 1.0 inches.

DRAWINGS

DESCRIPTION

Figure 1:
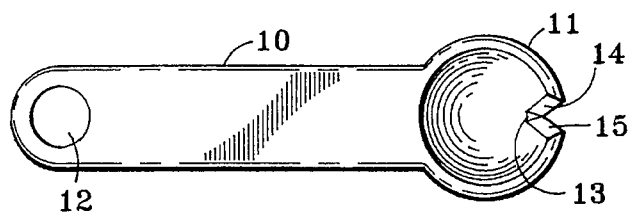
FIG. 1 is a plan view of the device.
Figure 2:
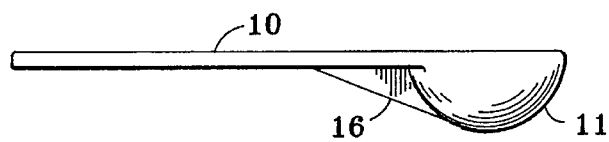
FIG. 2 is a side view.
Figure 3:
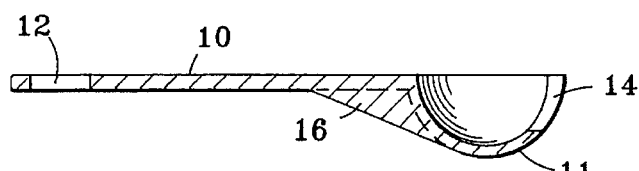
FIG. 3 is a cross section side view.
Figure 4:
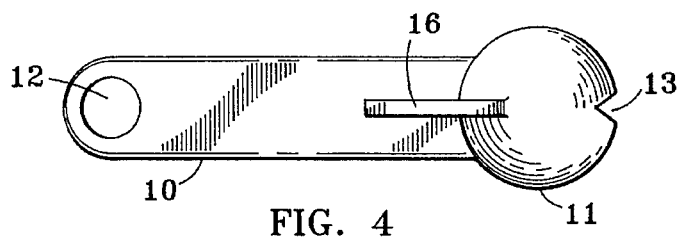
FIG. 4 is a bottom view.
Figure 5:
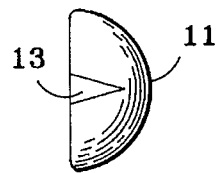
FIG. 5 is an end view of the scoop.

Referring to the drawings, FIGS. 1–5, the tick removing device of this invention comprises a handle, 10, at one end of which is a scoop, 11. At the other end of the handle is an opening, 12, so that a lanyard or the like may be attached.

The scoop can be of any convenient shape such as square with a broad leading edge, but it is preferred that it be oval or hemispherical so that the leading edge of the scoop in use flares away from the skin of the host leaving only a small contact area. The leading edge has a notch, 13, cut in it which is preferably V-shaped as shown. The inside, facing surfaces of the notch, 14 and 15, are preferably bevelled or flared in the range of 50 to 75 degrees to give the leading edge of the notch a sharp edge.

As previously indicated this device is quite small usually having an overall length in the range of three to five inches, e.g. 3.5 inches with the handle having a width of about ½ inch. The hemispherical scoop may have a diameter in the range of 0.4 to 1.0 inches e.g. 0.5 inches. The notch may open to an angle in the range of 20 to 35 degrees e.g. 25 degrees and extend downwardly with respect to the center of rotation of the hemispherical scoop 45 degrees from the upper edge of the scoop.

Figure 6:
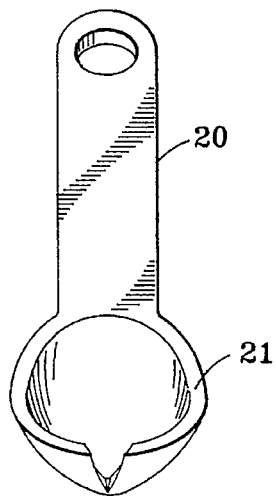
FIG. 6 is a perspective view of the device of this invention having an oval-shaped scoop or cup.

FIG. 6 shows the device, 20, of this invention with an oval-shaped scoop 21.

While the tick removing device of this invention can be stamped from a metal such as aluminum, it is preferred that it be made by injection molding a plastic in which case a reinforcing web, 16, may be placed behind the scoop as shown.

In use, once the tick has been isolated so the tick is clearly visible and free from obstruction, the cup is placed on the skin with the handle roughly perpendicular to the skin and with the wide part of the V encompassing the tick. A slight downward pressure is applied on the skin and the device is slid forward so that it surrounds the tick on three sides with the small part of the V framing the tick. A continuing of the forward sliding motion of the cup against the skin releases the tick entirely. None of the ticks mouth parts are left behind as the tick remover draws the tick upward from the skin. The tick is then removed from the host in the cup and can simply be tipped out of the cup and disposed of without need to touch it. Compared to other devises proposed for removing ticks it can be seen that there is no need to squeeze the tick which might rupture it or cause it to regurgitate.

Having described this invention, what is thought to be protected by Letters Patent is succinctly set forth in the following claims:

What is claimed is:

1. A device for removing a blood sucking parasite such as a tick from a host comprising:

a spoon-shaped member having a handle with a scoop at one end, said scoop having a rim and an outer end opposite said handle, said rim and said handle lying in the same plane and said outer end having a single notch therein of a size and shape for permitting the scoop at said notch to be moved laterally across the surface of the skin of the host and passed between said parasite and the skin with said handle roughly perpendicular to said skin until said notch engages the parasite underneath the parasite's body; the notch being sized and configured so as to extract the parasite by further lateral movement of the notch relative to the parasite.

2. The device of claim 1 wherein said scoop is hemispherical, wherein said notch is V-shaped with edges on either side, ends in an apex and extends from the rim of said scoop downwardly with said apex being approximately 45 degrees below said rim and wherein said notch opens to an angle in the range of 20 to 35 degrees.

3. The device of claim 2 wherein said edges are inwardly flared to an angle in the range of 50 to 75 degrees thus giving said notch sharp leading edges on either side.

4. The device of claim 2 wherein said scoop has a diameter in the range of 0.4 to 1.0 inches and the overall length of said device is in the range of 3 to 5 inches.

5. The device of claim 1 wherein said scoop is oval with a broader end and an opposite narrow end, said handle being attached to said narrow end.

6. A method of removing a tick from the skin of a host comprising taking in hand a device comprising a spoon-shaped member having a handle with a scoop at one end, said scoop having a rim and an outer end opposite said handle, said rim and handle lying in the same plane, and said outer end having a single notch therein of a size and shape to permit said scoop at said notch to be passed between said tick and said skin; aligning said notch with said tick with said handle roughly perpendicular to said skin; moving and sliding said device toward said tick and engaging the tick in said notch with said scoop being underneath the body of said tick; continuing said moving and sliding with the said scoop against said skin until said tick is released from said skin; removing said device from said host and disposing of said tick.

7. The method of claim 6 wherein said device has a length in the range of 3 to 5 inches wherein said scoop is hemispherical and has a diameter in the range of 0.4 to 1.0 inches, and wherein said notch has sharp leading edges on either side.

* * * * *